United States Patent [19]
Dorin et al.

[11] Patent Number: 5,466,781
[45] Date of Patent: Nov. 14, 1995

[54] PROCESS FOR PURIFYING BACTERIALLY PRODUCED M-CSF

[75] Inventors: Glenn Dorin, San Rafael; David R. Gray, El Cerrito; Byeong S. Chang, Orinda; Cynthia A. Cowgill; Robert J. Milley, both of Berkeley, all of Calif.

[73] Assignee: Chiron Therapeutics, Emeryville, Calif.

[21] Appl. No.: 28,375

[22] Filed: Mar. 8, 1993

Related U.S. Application Data

[63] Continuation-in-part of Ser. No. 705,399, May 24, 1991, abandoned.

[51] Int. Cl.$^6$ ............................ C07K 14/53; C07K 1/14; C07K 1/34; C12P 21/02
[52] U.S. Cl. .................. 530/351; 530/412; 530/414; 530/427; 435/71.1; 435/71.2; 435/69.5; 424/85.1
[58] Field of Search ...................... 530/351, 412, 530/414, 427; 435/71.1, 71.2, 69.5; 424/85.1

[56] References Cited

U.S. PATENT DOCUMENTS

| | | | |
|---|---|---|---|
| 4,572,798 | 2/1986 | Koths et al. | 530/351 |
| 4,929,700 | 5/1990 | Halenbeck et al. | 530/351 |
| 5,248,769 | 9/1993 | Darin | 530/414 |

FOREIGN PATENT DOCUMENTS

| | | | |
|---|---|---|---|
| 8910407 | 11/1989 | WIPO | 424/85.1 |

OTHER PUBLICATIONS

Yamanishi et al. "Renaturation, Purification & Characterization of Human Truncated MLSE Expressed in Escherichia coli" J. Biochem 404–409 1991.
Remingtons Pharmaceutical Scienes 17th Ed. 1985 pp. 1538–1539 "Freeze Drying".
Halenbeck et al "Purification & Characterization of Recombinant Human M–CSF & Generation of a Neutralizing Ab Useful for Western Analysis". J Biotechnol. 8:45–58 1988.
Halenbeck et al. "Renaturation & Purification of Biologically Active Recombinant Human MCSF Expressed in E coli Bio Technology". 7:(7) 1989 pp. 710–715.

*Primary Examiner*—Michael G. Wityshyn
*Assistant Examiner*—Nancy J. Degen
*Attorney, Agent, or Firm*—Ling-Fong Chung; Philip L. McGarrigle, Jr.; Robert P. Blackburn

[57] ABSTRACT

A process is described for producing M-CSF from bacteria. It includes: fermentation of bacteria containing M-CSF DNA; harvest of the fractions that contain the M-CSF protein (refractile bodies); primary recovery of the protein; solubilization and denaturation of refractile bodies; M-CSF refolding; purification by column chromatography and other methods; and formulation of the properly refolded M-CSF. This method is advantageous over prior methods in terms of yield and purity.

23 Claims, 1 Drawing Sheet

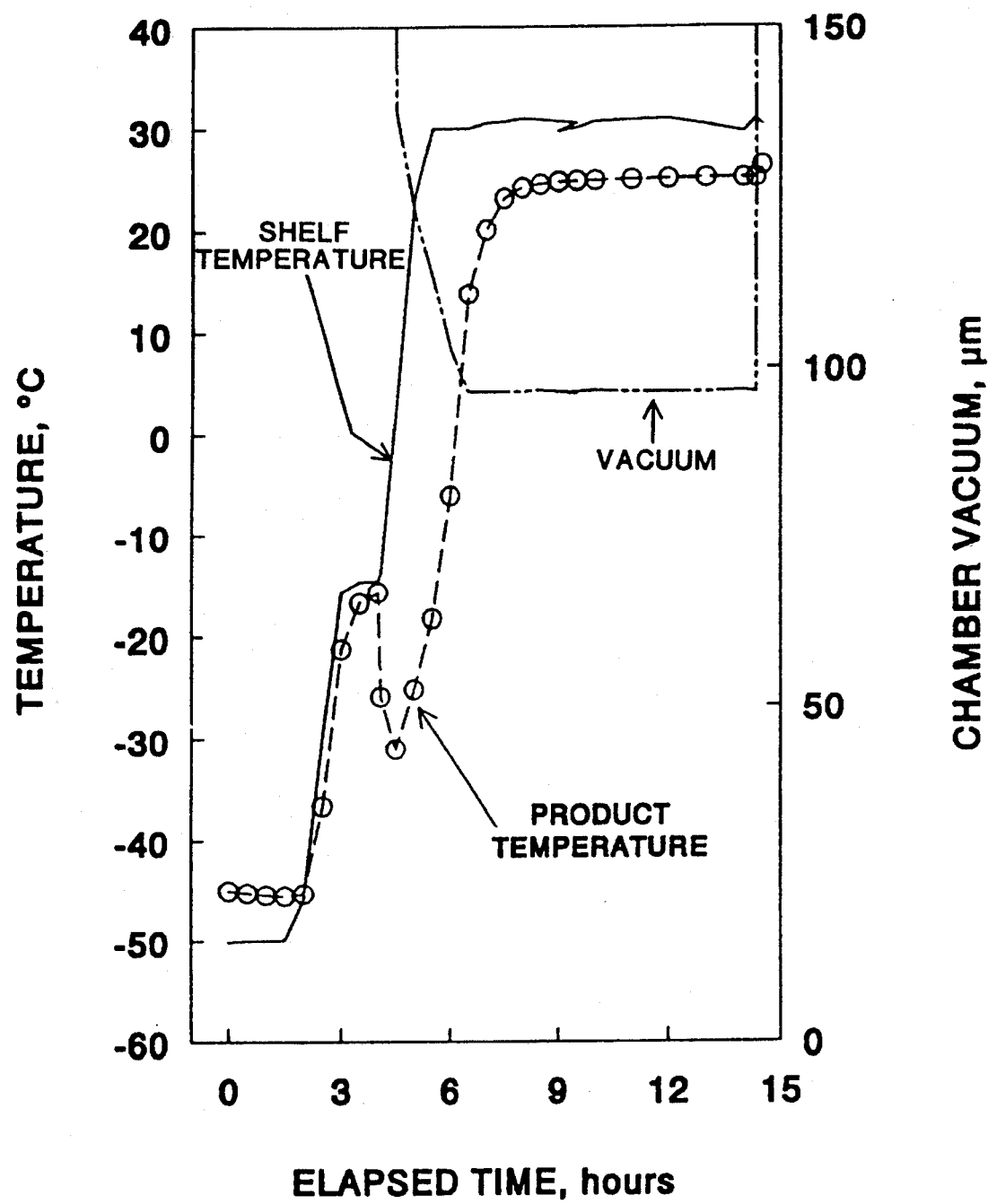

PROCESS FOR PURIFYING BACTERIALLY PRODUCED M-CSF

CROSS-REFERENCE TO RELATED APPLICATIONS

This application is a continuation-in-part of U.S. patent application Ser. No. 07/705,399, filed 24 May 1991 now abandoned.

FILED OF THE INVENTION

The present invention relates to a process for bacterially producing M-CSF. More specifically, the present process describes the following steps for producing M-CSF dimer: 1. Fermentation and Harvest; 2. Primary Recovery; 3. Solubilization and Denaturation of M-CSF Refractile Bodies; 4. Refolding-Oxidation; 5. Column Chromatography and Purification; 6. Formulation; and 7. Lyophilization.

BACKGROUND OF THE INVENTION

M-CSF is a protein which exhibits the spectrum of activity understood in the art for M-CSF, also known as CSF-1, i.e., when applied to the standard in vitro colony stimulating assay of Metcalf, D., *J. Cell. Physiol.* (1970) 76:89 as modified by Ralph et al., *Blood* (1986) 68:633, it is capable of stimulating the formation of primarily macrophage colonies. Native M-CSF is a glycosylated dimer; dimerization is reported to be necessary for activity as the M-CSF monomer is not active in the Metcalf or Ralph colony stimulating assays or various other in vitro bioactivity assays (Das, S. K. et al., 1981, *Blood* 58:630–641; Das, S. K. et al., 1982, *J. Biol. Chem.* 257:13679–13681; Stanley, E. R. et al., 1977, *J. Biol. Chem.* 52:4305–4312, Halenbeck, R. et al., 1989*Bio/Technology*, 7:710–715). The term "M-CSF" refers to proteins that have M-CSF activity in the assays described above and are substantially homologous to the native sequence. Examples of M-CSF sequences, a discussion of various deletion mutants, and processes for bacterial production are shown in U.S. Pat. Nos. 4,847,201 and 4,929,700 which are hereby incorporated by reference in their entireties. Generally, the term "M-CSF" can include M-CSF monomer, M-CSF dimer, or M-CSF refractile body. However, more specific terms, i.e., M-CSF monomer, will be used whenever possible. "M-CSF monomer" refers to a polypeptide comprising an amino acid sequence of a single subunit of an active M-CSF dimer. The amino acid sequence need not be identical to the M-CSF monomer sequences found in nature. Instead, the M-CSF monomer sequences may be routants and/or fragments of the naturally occurring M-CSF monomer sequences. However, M-CSF monomers can be folded and oxidized to form with another M-CSF monomer an active M-CSF dimer. "M-CSF dimer" refers to the biologically active dimer of M-CSF monomers. Biological activity of M-CSF dimers can be measured in any of the assays described above, Metcalf, Ralph et al., Das et al. (1981 & 1982), Stanley et al., and Halenbeck et al., supra. The size the M-CSF dimer can be measured by standard protein gels as described by Sambrook et al., infra.

To purify M-CSF dimer from human sources, such as urine, is very cumbersome. However, recombinant DNA technology has facilitated production of M-CSF dimer, and the pharmaceutical industry can bring such drugs to the public more efficiently without the need for expensive and dangerous human products. Expressing the protein is only part of the process of making a pharmaceutical. The protein must also be purified, refolded, if necessary, and formulated for storage. Methods for producing, purifying, refolding, formulating, and lyophilizing M-CSF dimer are described, for example, in U.S. Pat. No. 4,929,700 and WO89/10407.

As stated above, U.S. Pat. No. 4,929,700 discloses a process to produce and recover M-CSF from bacterial cells in a properly refolded form. U.S. Pat. No. 4,929,700 discloses the following process steps of: fermentation and harvest of the bacterial cells; primary recovery of intracellular pellets or aggregates containing M-CSF monomer, called "M-CSF refractile bodies" (M-CSF RB); solubilization and denaturation of M-CSF RB; refolding & oxidation; column chromatography and purification; and formulation. U.S. Patent '700 is relevant as background, because the present invention is an advantageous modification of this earlier process.

The present invention can purify and refold M-CSF monomers into M-CSF dimers from M-CSF RB which vary greatly in their physical characteristics. Generally, refractile bodies are porous aggregates of proteins that are produced by such organisms as *E. coli* or yeast. Other cell components, such as carbohydrates, may become associated with refractile bodies. The composition of these components can change depending on the health of the cells producing the refractile bodies, the growth conditions, or the cell harvesting conditions. For example, if the bacterial cells begin producing heat shock proteins, different cell metabolites may associate with the refractile bodies, and consequently, the refractile bodies may exhibit different physical characteristics. Also, when the bacterial cells are lysed, the media components or cellular components, lipids and DNA, for example, may become associated with the refractile bodies. Further, during front-end purification procedures, contaminants may associate with the harvested refractile bodies. Thus, such changes in the size, density, hydrophobicity, and other characteristics of the refractile bodies can create bottlenecks in the downstream processing and result in eventual loss of the desired proteins from the refractile bodies.

Once the protein is produced, refolded, and purified, formulation and lyophilization procedures are critical for long term maintenance of protein stability. Typical lyophilization schemes comprise a freezing step, a primary drying step, and a secondary drying step.

The formulation is frozen in order to:

(1) freeze the protein;

(2) freeze the unwanted water; and (3) form a matrix, to facilitate reconstitution of the protein.

During the freezing step, the formulation may undergo several temperature shifts to freeze and to properly crystallize the formulation components. See Williams et al., *J. Parent. Sci. Tech.* 38(2): 48–59 (1984), at page 49, bottom right column. These shifts in temperature are performed at normal atmospheric pressures, and thus, the formulation is not being dried during these temperature shifts.

The formulation is dried in two steps according to known lyophilization procedures. During both primary and secondary drying, the chamber pressure is reduced to force the water to proceed directly from solid to gas phase, i.e., sublimate. The primary drying begins after the formulation is frozen, and most of the water is removed by this step. During primary drying, the pressure in the sample chamber is reduced, and the shelf temperature of the lyophilizer is raised and held constant at a primary drying temperature. The shelf temperature is held constant to allow the product temperature to equilibrate with the shelf temperature as shown in FIG. 1 on page 49 of Williams et al., supra. The water vapor is discharged into the condenser of the lyophilizer, which re-freezes the vapor.

After primary drying is completed, again under reduced chamber pressure, the shelf temperature is raised to a secondary drying temperature and then held constant. Again, the shelf temperature is held constant to allow the product temperature to equilibrate with the shelf temperature. During secondary drying, water which is tightly bound to the product is removed.

One general formulation and lyophilization procedure for M-CSF dimer is described in WO89/10407 by Morris et al. This application relates to specific methods to reduce the number of aggregates of M-CSF after lyophilization. Morris et al., supra describes a method to circumvent such aggregation by:

(1) removing as many M-CSF aggregates as possible before formulation; and (2) adding a polyoxyethylenic non-ionic surfactant to the formulation.

Thus, WO89/10407 provides no motivation to modify known lyophilization procedures, but merely directs those skilled in the art to two pages from *Remington's Pharmaceutical Sciences* and the lyophilization procedure in Example 2 of the Morris et al. application. Neither citations suggest any innovation to known lyophilization procedures.

SUMMARY OF THE INVENTION

The present invention is an improved process of purifying M-CSF dimer from M-CSF monomer produced in the form of M-CSF RB in a microorganism. The process comprises the following steps:

1. Fermentation & Harvest;
2. Primary Recovery;
3. Solubilization & Denaturation of M-CSF RB;
4. Refolding & Oxidation; and
5. Column Chromatography, & Purification.

Specifically, the present invention is an M-CSF dimer purification process with an improved solubilization and denaturation step to increase the yield of "foldable" M-CSF monomer isolated from M-CSF RB. The fermentation, harvest, and recovery conditions can cause great variation in the physical and chemical characteristics of M-CSF RB. These variations can lower the yield of "foldable" M-CSF monomers, i.e., M-CSF monomers which can be folded into active M-CSF dimers. However, M-CSF monomer from various M-CSF RB sources can be folded into active M-CSF dimers if the following procedure is utilized when solubilizing and denaturing M-CSF RB:

exposing the harvested M-CSF RB to an effective amount of a guanidine salt to solubilize and denature the harvested M-CSF RB to produce M-CSF monomer mixture; and dialyzing the M-CSF monomer mixture to remove the contaminants, as measured by absorbance at 280 nm ($OD_{280}$ or $A_{280}$), that prevent folding of M-CSF monomers.

Also, the present invention is an M-CSF dimer purification process with an improved method of removing unwanted proteases, which inhibited refolding of the M-CSF monomer. The U.S. Pat. No. '700 processes utilized a DEAE column to remove unwanted bacterial proteases. This column step was performed after step 1, fermentation and harvest of the microorganisms containing M-CSF RB. Though, the DEAE column step was very efficient in removing the unwanted protease, an unnecessary amount of M-CSF monomers was lost. Further, the fewer columns needed; the more efficient a large scale purification process is. The present processes remove the unwanted proteases and nucleic acids by diafiltration of the harvested M-CSF RB from step 1 against an acetate/salt buffer using an effective filter with marginal loss of M-CSF RB. The combination of diafiltration step and a centrifugation step is also effective.

Additionally, the present invention is an improved M-CSF dimer purification process which increases the M-CSF RB yield when octanol is used to kill the viable microorganism expressing the M-CSF RB. Specifically, two improvements were made to the '700 process. First, the percentage of sucrose of the homogeneous sucrose cushion is lowered from 25% (wt/v) because after exposure to 1-octanol, the density distribution of the M-CSF RB is altered. As a result, the majority of 1-octanol treated M-CSF RB no longer pellet but float in the a 25% (wt/v) homogeneous sucrose cushion and are unrecoverable. The percentage of sucrose is lowered to increase the number of M-CSF RB that pellet. As a consequence of the lowered percentage of sucrose, the pelleted M-CSF RB contain a contaminant which causes a hazy precipitate or colloidal material during the refolding step. A wash step with non-ionic detergent was added after the homogeneous sucrose cushion step. This wash step removes the contaminant, residual 1-octanol, and other contaminants from the M-CSF RB.

Also, the present invention includes a process for lyophilizing a liquid M-CSF formulation, which includes:

a) freezing the liquid M-CSF formulation, comprising M-CSF dimer, an effective concentration of mannitol and an effective concentration of an amorphous protectant, to form a frozen product comprising an effective amount of crystallized mannitol;

b) drying the frozen product by raising the product temperature to a final product temperature without a constant drying period under subatmospheric pressures and maintaining the final product temperature.

Among other factors, the present process is an advantageous improvement over the prior process. Specifically, the present process: (1) allows a scale-up of '700 to produce M-CSF dimer in commercial quantities without any loss in purity; (2) allows M-CSF monomer to be refolded at higher concentrations (and at lower volumes); (3) produces a higher yield of M-CSF; and (4) removes damaging proteases earlier in the purification process so that they do not inhibit M-CSF dimer formation.

Specifically, we achieve benefits from resuspending M-CSF RB in 1% (v/v) Triton® X-100 and diafiltrating them against an acetate/salt buffer because we can more effectively purify M-CSF monomer from bacterial contaminants, such as non-proteinaceous components, proteases, nucleic acids, and residual octanol. Removing proteases earlier in the process allows us to postpone purifying the M-CSF by chromatography until after the M-CSF has been refolded. This purification process is further advantageous because we can subsequently refold the M-CSF monomer at higher concentrations which is advantageous because a scale-up of the '700 process would require very large refolding vessels.

Also, suspending the M-CSF RB in 12% (wt/v) homogeneous sucrose cushion is advantageous because octanol associated with M-CSF RB interferes with M-CSF RB recovery when 25% (wt/v) sucrose is used (as in the '700 process). Consequently, we receive an increased yield by decreasing the sucrose concentration.

Additionally, the present lyophilization process allows for more rapid and efficient lyophilization than prior art processes without unwanted aggregation and without loss of biological activity.

BRIEF DESCRIPTION OF THE DRAWINGS

The FIGURE depicts the shelf & product temperatures, and the chamber pressure during the claimed lyophilization process.

DETAILED DESCRIPTION OF THE INVENTION

A starting point for the present process is described in Halenbeck et al., U.S. Pat. No. 4,929,700 which is hereby incorporated by reference in its entirety. Unless otherwise noted, all the same definitions, ranges, conditions, concentrations, steps, orders, ingredients, etc., apply. The present invention is described by the steps below which include the times, temperatures, concentrations, pHs, and other variables that affect the process. It is understood that these variables may be adjusted to achieve the same process goals and that any adjustment would not necessarily remove another process from the present scope.

The present process produces a pure, correctly refolded and oxidized M-CSF dimer which is capable of formulation. It comprises the following steps which are correlated to scheme 1, on page 30: fermentation and harvest (step 1); primary recovery (steps 2-9); solubilization and denaturation of M-CSF RB (steps 10-12); refolding/oxidation, column chromatography and purification (steps 13-22); and formulation (steps 23-26). The following discusses preferred conditions in the present process.

I. Fermentation and Harvest

Microorganisms containing M-CSF RB can be produced by using known recombinant DNA techniques to produce an M-CSF monomer encoding expression vector and inserting it into a microorganism capable of expressing M-CSF RB. See Sambrook et al., MOLECULAR CLONING, A LABORATORY MANUAL, 2nd ed., Cold Spring Harbor Laboratory Press (1989) for such techniques.

Typically, an expression vector comprises an M-CSF monomer encoding gene and expression controlling components such as, a promoter, a terminator, selectable marker and origin of replication. Note, because the M-CSF is to be expressed intracellularly to produce M-CSF RB, a secretion leader is not necessary. The expression regulating components are well known to the art and can be constructed by either synthetic or cloning techniques. Also, these components can be purchased from commercial sources, such as Boeringher Mannhiem, for instance. The expression regulating components are chosen for convenience and optimization and will not affect the invention. M-CSF monomer encoding sequences can be cloned according to references such as '700, U.S. Pat. No. 4,847,201, by Kawasaki etal., and Sambrook et al., supra or by purifying such sequences from the ATCC deposit provided by Applicants. Preferably, the expression vector used for bacterial expression of M-CSF monomers that form M-CSF RB is pLCSF 221A.

Once the M-CSF monomer encoding expression vector is completed, it is inserted or transformed into the microorganism of interest. A number of bacterial or yeast cells can be used. Both types of cells will produce refractile or inclusion bodies. Preferably, E. coli cells are used, specifically strain DG116. Many transformation techniques are known for inserting expression vectors into bacterial cells. Sambrook et al. and Kawasaki et al., supra describe several known techniques. Applicants provide a preferred transformed E. coli cell line which is capable of expressing M-CSF RB. This cell line, named E. coli DGl116/pLCSF 221A, was deposited with the ATCC on 14 Apr. 1987 and assigned accession no. 67,390.

Because of the flexibility of the instant invention, neither the media components nor the fermentation conditions are critical, though these components and conditions can change the physical characteristics of M-CSF RB. Thus, the media for fermentation is chosen for convenience and optimization of the present invention. For large scale production, a large fermentor and minimal media components are desired.

For example, E. coli cells which have been previously transformed with DNA encoding M-CSF monomer, are grown in a 150 L or 1500 L fermentor (total of 100 L or 1000 L liquid). The fermentor contains water, trace elements 60 $\mu$M $ZnSO_4.7H_2O$, 60 $\mu$M $MnSO_4.H_2O$, 2 $\mu$M $CuSO_4.5H_2O$; 1.5 mM $Na_3$ citrate. $2H_2O$; 25 mM $KH_2PO_4$; 100 mM $(NH_4)_2$ $SO_4$; and 0.02% (v/v) media PPG (polypropylene gylcol). PPG is fed during the fermentation as required to control the foam. Typically, the amount of PPG consumed is about 1 L per 1000 L of media. The medium is sterilized in the fermentor, and the following ingredients are added aseptically to the following final concentrations: 100 $\mu$M $FeSO_4.7H_2O$; 3 mM $MgSO_4.7H_2O$; 20 mg/L thiamine. HCl; and 5 to 12 g/L glucose. For the 100 L scale, preferably, glucose is maintained at a concentration between about 2 to 12 g/L by continuous regulated feed. For the 1000 L scale, preferably, the glucose is added three times to a final concentration of 20 g/L at the onset, at induction, and some time between 1 and 4 hours after induction. Then, the fermentor is inoculated with E. coli DG116/pLCSF 221A (ATCC No. 67,390, deposited Apr. 14, 1987), a bacterium which contains a plasmid encoding a long form of M-CSF monomer (see U.S. Ser. No. 07/105,261). The fermentor is inoculated with approximately to give 2 mg/L of bacteria (dry weight) in the fermentor.

The culture is fermented at 30° C. and once the $OD_{680}$ reaches 25, the temperature is shifted to induce expression. ($OD_{680}$ and $A_{680}$ are used interchangeably. This is true with the other absorbances cited in this application.) This 25 $OD_{680}$ is the appropriate time point to shift the temperature in either the 100 L or 1000 L scale. Preferably, the temperature is shifted to between 37° C. and 40° C., more preferably 38.5° C. Casamino acids are added to a final concentration of 2% (wt/v) at induction (see U.S. Pat. Nos. 4,656,132 and 4,894,334, which are herein incorporated by reference in their entireties).

Preferably between 4 and 7 hours after induction, more preferably 6 hours, the cells are harvested by (1) concentration of the cells, and (2) removal of unwanted media components. Applicants have found that lowering the ionic strength of the media before lysing the microorganisms containing M-CSF RB eases the separation of unwanted nucleic acids and membrane components from M-CSF RB. The microorganisms are concentrated four fold by cross flow filtration with a 0.2 $\mu$m PTFE flat sheet membrane utilizing a transmembrane pressure differential of 10–50 psi. Further, unwanted media components can be removed and the ionic strength lowered by diafiltering the microorganisms containing M-CSF RB with a 0.2 $\mu$m PTFE flat sheet using a transmembrane pressure differential of 10–50 psi versus 5–10 volumes of 100 mM sodium citrate, 2 mM EDTA at pH 6.5 to 6.8. (This pH tends to keep the M-CSF refractile bodies insoluble during subsequent disruption because higher pH (>7.8) tends to solubilize M-CSF refractile bodies. Consequently, M-CSF monomer is prevented from being transferred into the supernatant, where it is lost.) The resulting diafiltered concentrate is called a cell paste.

II. Primary Recovery

The first step of primary recovery is disrupting and killing the microorganisms containing M-CSF RB. The term "isolating M-CSF RB" includes harvesting the microorganisms containing M-CSF RB and the first step of primary recovery. After disrupting the microorganisms containing M-CSF RB, the M-CSF RB can be subjected to further processing, such as solubilization and denaturation procedures, or can be subjected to further purification of whole M-CSF RB, such as isolation by homogeneous sucrose cushion, for instance.

Also, the primary recovery process comprises separating the M-CSF RB are separated from the unwanted cellular debris.

The microorganisms containing M-CSF RB can be disrupted by enzyme digestion, beads, or using a homogenizer. For example, the cell paste is subject to disruption by homogenization at 7500 psig, by either recycle mode or discrete pass mode (Preferably 3 passes at ~10°–15° C.).

Next, as a safety precaution, the remaining unlysed microorganisms containing M-CSF RB are killed. The cells may be killed using phenol, toluene, octanol, or formaldehyde, for example. 1-Octanol is the preferred reagent to kill *E. coli*. However, adding an "effective amount of 1-octanol" changes the density distribution of M-CSF RB. This change may be critical if the M-CSF RB are separated from unwanted cellular debris by density differences, which is the preferred method of separation. Preferably, a minimum of 1-octanol is used to kill the microorganisms containing M-CSF RB, and exposure to 1-octanol is minimized. Preferably, the lysed microorganisms containing M-CSF RB are incubated with an effective amount of octanol for at least one hour to kill the remaining whole cells. The time period may be longer. However, the length of time the M-CSF RB remain in the octanol may alter the distribution of densities unpredictably. Also, the specific time point which 1-octanol is added is carefully controlled. For example, 1-octanol may be added prior to, or at the same time as, the sucrose is added. Preferably, 1-octanol is added at the same time as the sucrose to minimize the M-CSF RB exposure to 1-octanol. Preferably, at least 0.5% (v/v), but no more than 2% (v/v) 1-octanol is effective for killing residual microorganisms, such as *E. coli*. More preferably, 1% (v/v) 1-octanol is added to kill residual *E. coli*.

Next, preferably the M-CSF RB are separated from the unwanted cellular components using an effective homogeneous sucrose cushion, though other methods can be employed, such as filtration. "An effective homogeneous sucrose cushion" is a homogeneous solution of sucrose of sufficient density that a substantial portion of M-CSF RB pellet and can be separated from a substantial portion of the unwanted cellular debris. Typically, at least 50% of the M-CSF RB; more typically, 60% of M-CSF RB; even more typically, 70% of the M-CSF RB sediment in the effective homogeneous sucrose cushion and can be separated from at least usually, 50% of the unwanted cellular debris; more usually, 60%; even more usually, 70% of the unwanted cellular debris. When this solution is centrifuged the desired component, M-CSF RB for example, will migrate in a from the unwanted components, cellular debris. In this case, preferably, the M-CSF RB sediment in the homogeneous sucrose cushion and are collected from the unwanted cellular debris. Factors which determine the effectiveness of the homogenous sucrose cushion include the concentration of sucrose, the centrifugal force, and the residence time, or flow rate.

The final concentration of the sucrose is critical. Preferably, the sucrose concentration is chosen such that the maximum yield of M-CSF RB sediment. Using 1-octanol may limit the percentage of M-CSF RB which will sediment. Thus, the sucrose concentration is optimized to increase M-CSF RB yield, which sediment in the homogeneous sucrose cushion. Preferably, sucrose is added to a final concentration between 10 and 15% (wt/v), preferably about 12% (wt/v), to achieve a suspension density which aids separation of the M-CSF RB, from the cellular debris. (We discovered that M-CSF RB are lost with increasing sucrose concentrations when octanol is used. Consequently, the sucrose concentration is lowered from the prior process to minimize M-CSF RB loss.)

The homogeneous sucrose cushion is centrifuged to sediment the M-CSF RB. Either a continuous flow or lab centrifuged can be used. If a lab centrifuge is used, the homogeneous sucrose cushion, preferably, is spun at 5,000 g for at least 40 minutes. Alternatively, if a continuous flow centrifuge is used the centrifugal force, the flow rate, and the type of centrifuge are critical. For example, preferably, the mixture is centrifuged at 7,000 g at a flow rate of 0.25 L/minute in a Westfalia KA2 centrifuge or in a Sharples AS16 centrifuge at 15,500 g at a flow rate of 2–3 L/min. If these centrifuges are used, then they must be stopped to collect the M-CSF RB from the centrifuge bowl. With a continuous flow centrifuge, the supernatant is continuously discharged. Other types of lab or continuous centrifuges may be utilized, and it is recognized that those skilled in the an can make the needed adjustments to centrifugal force and flow rate, for example, with these different centrifuges to produce an effective homogeneous sucrose cushion.

Utilizing a homogeneous sucrose cushion comprising less than 25% (wt/v) sucrose results in formation of a hazy precipitate or colloidal material during refolding of M-CSF monomers from the M-CSF RB. Applicants believe that the haziness lipid-like component, which contains no protein as measured by Bradford assay, such as that manufactured by Bio-Rad. To remove the contaminant which causes this effect, the M-CSF RB are washed in a non-ionic detergent, which can remove bacterial membrane components as well as the residual 1-octanol. The M-CSF RB are resuspended in an effective amount of non-ionic detergent solution, preferably the non-ionic detergent is Triton® X-100 in a concentration between 0.1% and 10% (v/v) Triton® X-100, more preferably about 1% (v/v) Triton® X-100. Also, preferably, the non-ionic detergent solution contains about 100 mM sodium citrate at pH 6.5. Resuspending the M-CSF RB in the non-ionic detergent solution aids to remove residual 1-octanol, nucleic acids, proteases, and non-proteinaceous material, and to improve purification, yield, and handling. (We find that using Triton® after the 12% (wt/v) sucrose step produces a clear liquid product later in the process.) To complete the wash, the non-ionic detergent solution is removed, preferably, by centrifuging the solution and removing the supernatant. For example, the M-CSF RB are centrifuged at about 5,000 g for at least 40 minutes in a lab centrifuge or in a Sharples AS16 centrifuge at 15,500 g at a flow rate of 2–3 L/min, and the M-CSF RB are recovered in the pellet phase. These centrifugation conditions are similar to those used to spin the homogeneous sucrose cushion. The pellet containing M-CSF RB is resuspended in the acetate/salt buffer, the diafiltration buffer of the next step.

Next, the M-CSF RB are resuspended and diafiltered against an acetate/salt buffer to effectively remove the unwanted bacterial proteases without the urea DEAE column in '700. Applicants found that diafiltration alone or in combination with a supernatant removal step is very effective to remove the unwanted bacterial proteases. This diafiltration step is also efficient method of removing the nucleic acids from the M-CSF RB.

By choosing the appropriate buffers, membrane pore size, membrane symmetry, and material of construction, greater than 95% of the protease activity, measured by a colormetric assay can be removed by diafiltration. The colormetric assay utilizes chromogenic substrates for serine protease, such as S-2222+S-2223, by Helena Labs, and measures absorbance at 405 nm ($A_{405}$), which indicates the pNP (para-nitrophenol) released from the substrates by serine protease activity. Applicants experiments on a small scale indicate that 1.0 and 2.0 micron hydrophilic PVDF membranes are the most efficient. However, these membrane are difficult to obtain for large scale production. Applicants found that diafiltering with a smaller pore membrane and removing the supernatant by a centrifugation step is just as effective for isolating the M-CSF RB from the bacterial proteases. For larger scale production, the supernatant containing the bacterial proteases can be removed from the M-CSF RB by an ultrafiltration and concentration step.

Preferably, the M-CSF RB are diafiltered using a 0.2 μm mixed cellulose ester hollow fiber membrane with transmembrane pressure differential of 5–20 psi, more typically, 10 psi. The M-CSF RB are diafiltered against at least 5 volumes, more preferably at least 7 volumes, even more preferably, at least 10 volumes of an acetate/salt buffer. The low pH of the acetate/salt buffer in conjunction with the high salt concentration serves to separate the positively charged proteins from the nucleic acids, which then are removed during the diafiltration. For example, the M-CSF RB are resuspended in about 50 mM sodium acetate, 0.5M NaCl, and 2 mM EDTA at pH 6.0, and the M-CSF RB are diafiltered against 10 volumes of the acetate/salt/EDTA solution to remove the proteases, Triton® X-100 and some nucleic acids. Next, for the 100 L scale, the M-CSF RB are recentrifuged at 4,000 g in a Sorval RC-3B centrifuge for about 40 minutes and the supernatant is removed to produce an M-CSF RB paste. For the 1000 L scale, the unwanted supernatant is removed by a ultrafiltration concentration step. The diafiltered M-CSF RB are concentrated 3 to 8 fold, preferably 5 fold, in the same configuration as the diafiltration. This step is a polishing step which removes more of the unwanted proteases from the soluble phase. This final M-CSF RB paste can be stored at − 70° C.

The benefits from resuspending the RBs in 1% (v/v) Triton® X-100 and the diafiltration against an acetate/salt buffer are that we can more effectively purify M-CSF from non-proteinaceous material, proteases, and nucleic acids, and it allows us to eliminate a low yield step in '700 (the DEAE column). Also, the increase in M-CSF yield increases the M-CSF to nucleic acid ratio. Furthermore, we can increase the M-CSF monomer refolding concentration from 0.2 $A_{280}$ to 1 $A_{280}$. Additionally, suspending the M-CSF RB in 12% (wt/v) homogeneous sucrose cushion is advantageous because octanol interferes with M-CSF RB recovery when 25% (wt/v) sucrose is used (as in the '700 process). Consequently, we receive an increased yield by decreasing the sucrose concentration.

III. Solubilization and Denaturation of RB

Next, the M-CSF RB are solubilized and denatured, so that the resulting M-CSF monomer can be oxidized and refolded to form an M-CSF dimer. Typically, M-CSF RB are exposed to an effective amount of a chaotrope during this step. In addition to the solubilizing and denaturing effects, the chaotrope also facilitates subsequent removal of other contaminants which prevent M-CSF monomers from folding into M-CSF dimers. Thus, removal of these contaminants increases the yield of "foldable" M-CSF monomer.

The M-CSF RB paste is thawed and solubilized in an effective amount of a chaotrope and the necessary buffer reagents. A preferred chaotrope is a guanidine salt, preferably guanidine hydrochloride. An effective amount of guanidine salt solubilizes and denatures the M-CSF RB to form a M-CSF monomer mixture and solubilizes the $A_{280}$ contaminant, which inhibit M-CSF dimer formation. For instance, the M-CSF RB paste can be solubilized in about 8M Urea, but a preferred solubilization solution contains 6M guanidine hydrochloride with the following buffer reagents: 5 mM dithiothreitol (DTT), 25 mM EDTA, 0.1M Tris at pH 8.5. Preferably, the Tris-base is added in its crystalline form to prevent further dilution of the M-CSF RB paste. EDTA is added to the solubilization solution to scavenge metal ions that may promote unwanted oxidation. Dithiothreitol is a reducing agent and aids in denaturing M-CSF RB and helps to maintain M-CSF monomer in a reduced, soluble form. The M-CSF RB paste can be suspended with a homogenizer, though such a step is not necessary. The M-CSF RB paste is incubated in the solubilization solution at 21°±° C. for at least 45–60 minutes to ensure adequate solubilization and denaturation.

The resulting M-CSF monomer mixture from the solubilization and denaturation of M-CSF RB can be subjected next to anion exchange chromatography to remove the nucleic acids. Salts may also be added to the solubilization solution to increase the conductivity of the M-CSF proteins. This increased conductivity may be useful in the anion exchange chromatography step.

The resulting M-CSF monomer mixture is sterile filtered before anion exchange chromatography. For this step, DEAE Zeta-Prep cartridges are preferred, but other resins that can be used are: PEI (polyethylene imine) sold by FMC Corp; DEAE resin, sold by Pharmacia, for example; and CDR (cell debris remover) sold by Whatman Biochemicals. When these resins are used at an increased ionic strength, the nucleic acids stick to the resin, and the M-CSF monomer passes through the column. This step removes residual nucleic acids and is more advantageous than the DEAE step shown in '700, when run at a higher throughput, because more M-CSF monomer was lost in the old process. This new step increases the ratio of M-CSF to nucleic acids, for example the plasmid DNA concentration is reduced two fold. Specifically, DEAE Zeta-Prep separation in 50 mM NaCl, 8M Urea, 12.5 mM EDTA, 5 mM DTT, 50 mM Tris at pH 8.5 is preferred. Instead of the anion exchange column step, preferably, the higher molecular weight DNA is removed by ultrafiltration with a 300 kD MWCO membrane after the secondary oxidation. This diafiltration is also preferred because step also removes high molecular weight M-CSF aggregates, which can lower M-CSF dimer yield in the subsequent column steps. This filtration step eliminates the need for the DEAE column, making the process more efficient on a large scale.

It is preferred that the M-CSF monomer mixture is dialyzed or diafiltered to remove the contaminants that prevent M-CSF monomers from folding into M-CSF dimers. Applicants believe that the contaminant can be detected by observing the absorbance at 280 nm ($A_{280}$). The diafiltration of the M-CSF monomer mixture reduces the $A_{280}$ value of the initial M-CSF monomer mixture by half. $A_{280}$ is a means for measuring the protein concentration of a solution. As confirmed by sizing HPLC, the protein concentration contributes only to part of the measured $A_{280}$ value. This may also be confirmed by other protein assays, such as gel analysis of Lowry assay. Applicants concluded that the diafiltration step removes a guanidine soluble, non-proteineous contaminant that can be detected at $A_{280}$, which inhibits M-CSF dimer formation. The combinations of these assays will indicate the amount of contaminant present. Because the contaminant prevents proper refolding, its absence can also be monitored by the yield of M-CSF dimer. Applicants found after this diafiltration step, that the final yield of M-CSF dimer increased from 40% to 70%.

In addition, removal of guanidine hydrochloride is preferred during the diafiltration process, because M-CSF monomers do not fold efficiently when exposed to this chaotrope. However, M-CSF monomers must be exposed to an effective amount of another chaotrope, preferably urea, and an effective amount of reducing agent for M-CSF monomers to fold into active dimers. Thus, usually, guanidine hydrochloride is removed of the M-CSF monomer mixture by diafiltration and replaced with an urea/reducing agent buffer.

Typically, the M-CSF monomer mixture is diafiltered using a 30 kD MWCO membrane. Regenerated cellulose is a preferred membrane material, but other materials such as polysulfone are just as effective. Further, the M-CSF monomer mixture is preferably diafiltered using by cross-flow filtration with a plate and frame diafiltration configuration. Applicants carefully chose the membrane pore size to minimize the loss of M-CSF monomer but maximize the throughput time. The pore size is larger than the M-CSF monomer, but only 10% of the M-CSF monomer is lost. Without being bound by theory, Applicants theorize that a guanidine soluble, non-proteineous contaminant is sticking to the membrane and decreasing the pore size. Preferably, the M-CSF monomer mixture is diafiltered against three different buffers. As a result of this diafiltration process, the final yield of active M-CSF dimer increases from 40 to 70%.

The first buffer the M-CSF monomer mixture is diafiltered against is a guanidine salt/reducing agent buffer. This first diafiltration buffer maintains the M-CSF monomer in a reduced, soluble form. Also, the first diafiltering buffer permits removal of guanidine soluble, non-proteineous contaminants. Applicants theorize, without being bound by such theory, that these contaminants prevent M-CSF monomer from refolding into M-CSF dimer. A chelating agent can also be added to the first diafiltration buffer. The chelating agent scavenges metal ions, which may cause unwanted oxidation. A high pH helps to keep the M-CSF monomer soluble. Preferably, the M-CSF monomer mixture is first diafiltered against at least a minimum of 2.3 volumes of 6M guandine hydrochloride, 5 mM DTT, 10 mM EDTA, 50 mM Tris pH 8.5 using the above filtration configuration.

The second diafiltering buffer lacks a guanidine salt, but contains a reducing agent to maintain M-CSF monomer in a reduced, soluble form. Preferably, the concentration of the reducing agent is lower in the second diafiltration buffer than the first diafiltration buffer. The presence of the reducing agent is only to maintain a state of reduction of the M-CSF monomer, and a high concentration of reducing agent is not needed promote reduction of disulfides. Further, the preferred reducing agent is DTT, and the concentration of DTT is preferably lowered in this diafiltration step in preparation for the refolding reaction where the DTT concentration is preferably below 250 µM.

A guanidine salt is not included in the second buffer because M-CSF monomer does not refold efficiently into M-CSF dimer in the presence of a guanidine salt. However, the presence of another chaotrope, such as urea, is necessary for efficiently refolding. Such a chaotrope may be added to the second diafiltration buffer; thus circumventing the need for the third diafiltration. Applicants have found that at a small scale the M-CSF monomer refolds more efficiently into M-CSF dimer when the M-CSF monomer mixture is first diafiltered against a non-denaturing buffer, without a chaotrope, and then into a denaturing buffer, containing a chaotrope. The M-CSF monomer mixture is diafiltered against at least 2.3, preferably, 2.5 volumes of a second diafiltration buffer of 3 mM DTT, 10 mM EDTA, and 50 mM Tris pH 8.5 using the above filtration configuration.

The third diafiltration buffer contains at least a chaotrope, preferably urea, and a reducing agent. A chelating agent, such as EDTA, can also be included to bind metal ions that can promote unwanted oxidation. A buffer is also preferred to maintain a high pH to keep the M-CSF monomer in its reduced, soluble form. The M-CSF monomer mixture is subjected to a third diafiltration step to incorporate the proper concentration of urea to the mixture without increasing the volume of the M-CSF mixture. Adding solid urea would increase the volume which may be unwanted if the refolding reaction vessel size is limited. Finally, the M-CSF monomer mixture is diafiltered against at least 2.3, preferably, 2.5 volumes of 8.67M Urea, 3 mM DTT, 10 mM EDTA, and 50 mM Tris pH 8.5 using the above filtration configuration.

IV. Refolding-Oxidation

M-CSF monomers resulting from the solubilizing and denaturing M-CSF RB, can be refolded and oxidized into biologically active dimers in a wide range of conditions, as shown in '700.

Large scale manufacturing has two major concerns: (1) maximizing throughput; and (2) minimizing the resources utilized. An efficient bench scale process may not be cost effective when scaled up linearly. Thus, the process steps of the this invention may vary depending on the equipment and material that are available and cost effective. For example, M-CSF monomer may be refolded at a concentration as high as 1 mg/ml because the process removes contaminants to such a level that refolding is minimally inhibited. This concentration is preferred when the reaction vessel volume and buffer material are limited. However, the yield of M-CSF dimer is higher when M-CSF monomer is refolded at a lower concentration such as 0.1–0.2 mg/ml. If a larger refolding reaction volume is feasible, preferably M-CSF monomer is refolded at these lower concentrations.

Typically, for refolding and oxidizing, the M-CSF monomer mixture is added to a final concentration $A_{280}$ between 0.2 and 2, more preferably between 0.75 and 1.5, most preferably about 1 to a redox buffer of 0.4 mM reduced glutathione, 0.2 mM oxidized glutathione, 50 mM Tris-HCl, 5 mM EDTA, at pH 8.5. The M-CSF monomer mixture is mixed with the redox buffer until, preferably, the final M-CSF monomer/redox mixture contains less than 250 nM DTT. Typically, the dialyzed M-CSF monomer mixture is added to the redox buffer to be diluted by a factor of 1/20. Preferably, the M-CSF monomer mixture pumped into the appropriate volume of redox buffer at a flow rate between 8–12 ml/min. The M-CSF monomer/redox mixture is incubated at 2°–8° C. for 1–5 days, preferably 4 days for maximal refolding, oxidation, and to maximize the yield of M-CSF biological activity. The present refolding step is advantageous because the total refolding volume is substantially less than with the '700 process. This ability to refold at a lower volume is advantageous because it allows us to use smaller vessels and less buffer in the process; a scale-up of the '700 process would require a 350 L vessel. The product of this oxidation step is an M-CSF pool. The M-CSF pool contains active M-CSF dimers, as well as higher molecular weight M-CSF oligomers. Though most of the M-CSF monomers were oxidized as a result of the first oxidation step, preferably, the M-CSF pool is subjected to a second oxidation step to drive the reaction to completion. Applicants believe that free sulhydryls can catalyze M-CSF aggregate formation, which results in loss of M-CSF dimer.

Consequently, after the primary oxidation step, the pH is adjusted to 6.8 to 7.2, preferably 7.0, with 1M $Na_2PO_4$ and 1N HCl. Preferably, the M-CSF pool is concentrated to an $A_{280}$ of 2 to 10, preferably to $A_{280}$ of 5 and diafiltered to remove the chaotrope and the primary redox buffer components, lower the pH, and suspend M-CSF pool in 20 mM $NaPO_4$, pH 7.0. This change in buffer is achieved by diafiltering the resulting M-CSF pool, preferably, with a 10 kD hollow fiber, polysulfone or regenerated cellulose, with a pressure difference of 15–20 psi against not less than 7 volumes of 20 mM $NaPO_4$ pH 7.0, more preferably not less than 10 volumes. The resulting M-CSF pool is oxidized a second time overnight at 4° C. by adding $CuCl_2$ to a final concentration of 0.2 mM (see U.S. Pat. No. 4,572,798 which relates to IL-2, but which also applies here, it is incorporated by reference in its entirety).

After the secondary oxidation, the M-CSF pool is ultrafiltered to remove the higher molecular weight DNA and M-CSF aggregates. Preferably, the M-CSF pool is ultrafiltered using a 300 kD MWCO membrane of polysulfone using a plate and frame configuration with a pressure differential of 15–20 psi. Regenerated cellulose membranes can be used in place of polysulfone membranes. After the ultrafiltration, the remaining M-CSF pool in the filtration device is diafiltered against 10 volumes of 20 mM $NaPO_4$. The low pH of the 20 mM $NaPO_4$ buffer protonates the sulfhydryls and prevents unwanted disulfide exchange and loss of M-CSF dimer during the subsequent chromatography steps in large scale production.

V. Column Chromatography and Purification

After the M-CSF monomers are refolded and oxidized to form M-CSF dimers, column chromatography, ammonium sulfate precipitation, and some additional steps are used to separate the unwanted oligomer and unwanted conformers and other contaminants from the M-CSF dimers.

The ultrafiltered M-CSF pool that was subjected to secondary oxidation loaded onto a DEAE-Sepharose® ion exchange column, equilibrated with 20 mM $NaPO_4$, pH 7.0. Protein is eluted from the column with a 0.0–0.4M NaCl linear gradient in 20 mM $NaPO_4$ at pH 7.0. The fractions containing proteins the size of M-CSF dimer are retained based on molecular weight cutoff and/or M-CSF biological assay. These fractions contain M-CSF dimers and oligomers and are subjected to ammonium sulfate precipitation to remove the unstable M-CSF conformer, residual monomer, and oligomers from the active M-CSF dimers. Ammonium sulfate, $(NH_4)_2SO_4$, is added to a final concentration between 1.0 and 1.3, more preferably of about 1.2M. Preferably, the M-CSF mixture is filtered with two filters, 1.2 and 0.45 μm, sandwiched together to remove the precipitants, and the filtrate is loaded onto a phenyl-Sepharose® column, equilibrated with 10 mM $NaPO_4$, pH 7.0 with 1.2M or preferably with 0.8M $(NH_4)_2SO_4$. The M-CSF dimer is eluted from the column equilibrated with $1.2M(NH_4)_2SO_4$, 10 mM $NaPO_4$ with a 1.2 to $0.0M(NH_4)_2SO_4$ linear gradient in 10 mM $NaPO_4$ at pH 7.0. Or the M-CSF dimer can be preferably, eluted from a column equilibrated with $0.8M(NH_4)_2SO_4$, 10 mM $NaPO_4$ with a 0.8 to $0.15M(NH_4)_2SO_4$ linear gradient. The fractions containing M-CSF dimer are sterile filtered. Next, the resulting M-CSF dimer filtrate is subjected to diafiltration with a 10 kD hollow fiber polysulfone membrane using a pressure differential of 15–20 psi against not less than 7 volumes, preferably not less the 10 volumes of sodium citrate at a concentration of between 6.0 and 6.5 mM, preferably at a concentration of 6.25 mM and at pH between 7.0 and 6.0, preferably at a pH of 6.5. The product from the diafiltration is called the purified M-CSF pool.

V. Formulation

The purified M-CSF dimer is formulated by adding the appropriate sterile components to the purified M-CSF pool. The formulation components should protect the M-CSF dimers during all stages of storage and use, i.e. when M-CSF dimers are in liquid solution, frozen, and lyophilized forms. The frozen or lyophilized forms of the formulation present special problems because these forms are not a homogenous mixture as the liquid form. Without being bound by theory, it is hypothesized that the frozen formulation contains protein-rich aqueous concentrates interspersed between ice and mannitol crystals. Under these conditions, proteins have a tendency to aggregate. Therefore, without being bound by the theory, one might expect the M-CSF dimers to aggregate under these conditions. Thus, it is preferred that the purified M-CSF dimer is formulated with an amorphous buffer and an amorphous protectant in addition to a crystallizing sugar. The amorphous components should remain with the M-CSF dimers and serve their functions more efficiently because they remain amorphous and therefore associate with the M-CSF dimer deposits under freezing conditions. Typically, the total percentage (wt/v) of solids in liquid M-CSF formulation will not exceed 10%. Typically, the total percentage (wt/v) of solids in a liquid M-CSF formulation will not exceed 10%.

Though the other components, such as the buffer and protectants, will remain amorphous under freezing conditions, a crystallizing sugar is preferred in the formulation. A crystallizing sugar, such as mannitol, creates a matrix when frozen, and a solid cake when freeze-dried. This cake greatly facilitates hydration of the MCSF dimer during necessary reconstitution procedures. Thus, the liquid M-CSF formulation should contain an effective concentration of mannitol. An effective concentration of mannitol is at least 1% (wt/v); and more typically, at least 3% (wt/v). Also, usually the concentration of mannitol in the formulation is no more than 10% (wt/v); and more usually no more than 5% (wt/v).

The liquid M-CSF formulation contains M-CSF dimers at a concentration of at least 1 mg/ml of M-CSF dimers; more typically, at least 3 mg/ml; even more typically at least 5 mg/ml. Also, usually, the liquid M-CSF formulation contains M-CSF dimers at a concentration no more than 25 mg/ml; more usually, no more than 15 mg/ml; even more usually no more than 10 mg/ml.

Examples of amorphous protectants are sucrose, dextran, trehalose, 2-hydroxypropyl-β-cyclodextrin, or glycine. These protectants help reduce the physical and chemical alterations to the M-CSF dimers, such as oxidation, etc. Preferably, M-CSF dimers are formulated with sucrose and glycine. An effective amount of amorphous protectant will prevent unwanted aggregation, chemical linkage, oxidation and degradation of M-CSF dimer. Too much amorphous protectant will hinder efficient lyophilization, and too little will reduce the shelf life of lyophilized M-CSF dimer.

Sucrose is usually added to the liquid M-CSF formulation to a final concentration of at least 0.1% (wt/v), more usually at least 0.75% (wt/v). Typically, the sucrose concentration in the formulation is no more than 2% (wt/v), more typically no more than 1.25% (wt/v).

Usually, glycine is added to the liquid M-CSF formulation to a final concentration of at least 0.01% (wt/v), more usually at least 0.3% (wt/v). Preferably, the glycine concentration in the formulation is no more than 1% (wt/v), more preferably no more than 0.7% (wt/v).

Buffers maintain the pH of the M-CSF dimer during lyophilization, storage, and once the M-CSF dimer is reconstituted. Maintenance of pH is critical to prevent such physical and chemical alterations, such as oxidation, during storage of the M-CSF dimer. The pH will be chosen not only to optimize the longevity of the M-CSF dimer but to ease administration of the M-CSF dimer to humans. Usually, the pH of the formulation is usually adjusted to between 6.0 and 7.5 with NaOH if a sodium containing buffering reagent is used. More preferably the pH is adjusted to 6.5.

A preferable amorphous buffer, such as sodium citrate, is added to the formulation to a final concentration of at least 1 mM, and more preferably at least 4 mM. Typically, the concentration of sodium citrate in the formulation is no more than 10 mM, and more typically no more than 6 mM.

Preferably, the liquid M-CSF formulation is sterile filtered before lyophilization.

VI. Lyophilization

The liquid M-CSF formulation may lyophilized according to techniques known in the art. However, because lyophilization processes are sensitive to formulation components, the following lyophilization technique is preferred with the above formulation components and concentrations. This lyophilization process comprises one freezing and one drying step.

A liquid formulation is usually freeze-dried in a lyophilizer, which includes a sample chamber with a shelf to place samples on, a means for adjusting the shelf temperature, a means for reducing the sample chamber pressure, and a condenser. See *Remington's Pharmaceutical Sciences*, p. 1538 (17th ed., 1985). In the lyophilizer, the temperature of the sample, whether a liquid formulation or a frozen product, is controlled by adjusting the shelf temperature. Freezing the liquid M-CSF formulation to form a frozen product, according to the instant invention, occurs under normal atmospheric pressure and can be done in the lyophilizer under normal chamber pressure or in an ordinary freezer. The drying step must occur under reduced sample chamber pressure for the water in the frozen product proceed directly from the solid to gas form.

The instant lyophilization process can freeze-dry M-CSF dimers without causing unwanted aggregation or loss of biological activity without adding a polyoxyethylenic nonionic surfactant, as Morris et al. suggested in WO89/10407. By ensuring that an effective amount of mannitol is crystallized during the freezing step, the instant lyophilization procedure can be used without forming unwanted M-CSF aggregation. When less than an effective amount of mannitol is crystallized, the frozen product must be dried below –40° C. for the water to sublimate. If the frozen product without an effective amount of crystallized mannitol is dried at a higher temperature, the water will evaporate from the product and inactivate the M-CSF dimers.

Once an effective amount of mannitol is crystallized, the shelf temperature can be raised to the final shelf temperature. The frozen product is allowed to equilibrate only at the final shelf temperature, unlike typical lyophilization schemes where the frozen product equilibrates with a primary and secondary shelf temperature. See FIG. 1 on p. 49 of Williams et al., *J. Paren. Sci. Tech.* 38(2): 48–59 (1984). Surprisingly, despite the sharp rise in temperature during the instant lyophilization procedure, water from the frozen product is sublimated, not evaporated, and the M-CSF dimers remain active. With this lyophilization process, liquid M-CSF dimer formulations can be freeze-dried more quickly without loss of biological activity.

Specifically, the liquid M-CSF formulation is first frozen at a temperature between –40° C. and –60° C. During this freezing step, most of the water crystallizes, however, a fraction of the mannitol does not. To ensure that an effective amount of mannitol crystallizes, the product temperature is raised to between –25° C. and 12° C. for at least 30 minutes, more preferably for at least one hour. This temperature range was chosen because at approximately –27° C., mannitol is known to crystallize from its frozen vitreous or glass form. During this freezing step, the pressure in the sample chamber is not reduced, and no sublimation of water or drying of the product occurs.

Typically, the liquid M-CSF formulation or frozen product temperature is adjusted by changing the shelf temperature of the lyophilizer. The sample temperature, whether the sample is solid or liquid, usually lags behind the shelf temperature. The sample temperature can be changed to a target temperature by two techniques. First, the shelf temperature may be changed and held constant at a target temperature until the sample equilibrates with the shelf temperature. Or the shelf temperature can be adjusted slowly to a target temperature so that the temperature difference between the shelf and the sample is minimal. Either method is effective for changing the sample temperature. The choice of techniques will depend on the desired rate of temperature change. However, the temperature should not be increased so quickly that the water evaporates instead of lyophilizes from the product.

Drying of the frozen product begins after an effective amount of mannitol has crystallized. The pressure in the sample chamber is reduced to below "subatmospheric pressures." Subatmospheric pressures refer to any pressure below one atmosphere unit. Preferably the subatomspheric pressure will between 500 and 10 μmHg; more preferably between 400 to 50 μm Hg; even more preferably between 200 and 100 μmHg.

Also, to dry the frozen product, the shelf temperature is increased rapidly to a final product temperature between 20° C. and 40° C., more preferably to a final product temperature between 25° C. and 35° C. The frozen product temperature is raised to a final product temperature "without a constant drying period" if the product temperature equilibrates or is held constant only at the final product temperature and is not maintained or held constant at any other temperature for substantial length, e.g. less than five minutes. For example, a constant rate of increase of temperature will be considered to lack a constant drying period. Preferably, the product is raised to a final product temperature of 30° C. at a rate of about 45° C. per hour. Typically, the shelf temperature is held at a final product temperature between 20° and 40° C. to allow the freeze-dried product to equilibrate to this temperature.

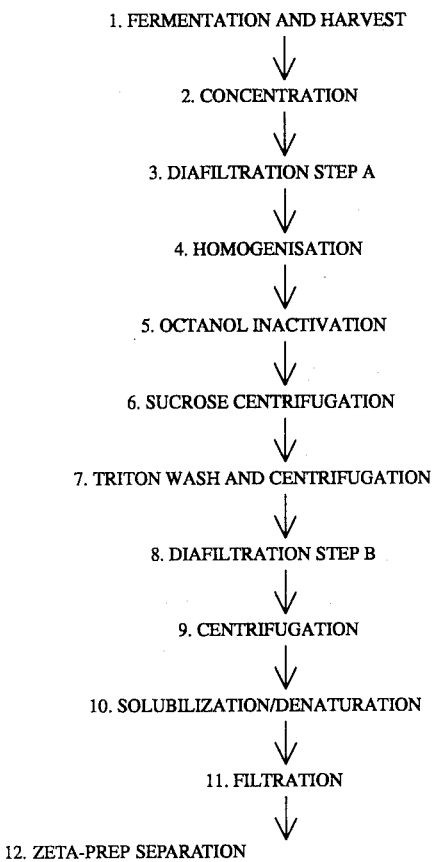

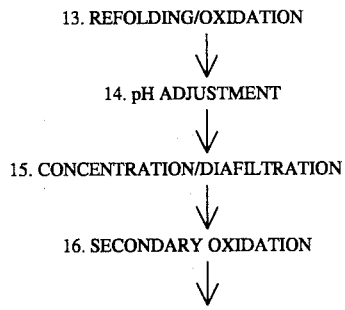

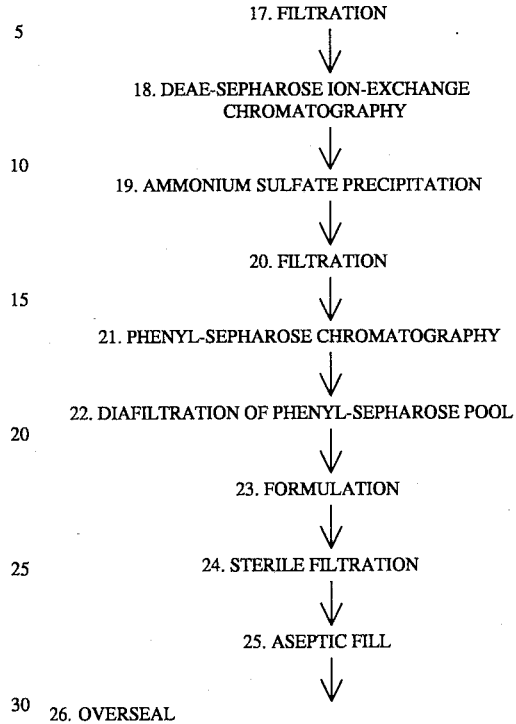

The present invention will now be illustrated by reference to the following examples which set forth particularly advantageous embodiments. However, it should be noted that these embodiments are illustrative and are not to be construed as restricting the invention in any way.

Example 1

Preparation of RBs According to '700

M-CSF RBs were prepared according to the prior process shown in Example 5 of U.S. Pat. No. 4,929,700. However, a Westfalia KA 2 centrifuge was used in lieu of the Westfalia SB7 centrifuge shown in '700 at Col. 17, line 37

Example 2

Preparation of RBs According to the Present Process (100 L)

This is an example of process steps 1 through 9 as shown in scheme 1, on page 30, and is called the upstream process.

The process scheme is illustrated in FIGS. 1 and 1A. E. coli DG116 containing plasmid pLCSF221A were grown at 30° C., induced at 37° C. at an $OD_{680}$ of 25 and harvested 6 hours post-induction. Nutrient concentrations and other fermentation details are essentially similar to those described in text above. The cells were chilled to 15° C. and concentrated to 20% of the original volume by microporous cross-flow filtration. The residual fermentation broth containing divalent cations was removed in the subsequent diafiltration against 180 L of 100 mM citrate, 2 mM EDTA, pH 6.5 in the same diafiltration system. The diafiltered suspension was homogenized at 7500 psig in a CD30 gaulin homogenizer in the recycle mode. The homogenate was made 1% v/v 1-octanol to inactivate residual live recombinant E. coli cells and kept overnight at 15° C. The treated homogenate was made 12% (wt/v) in sucrose and centrifuged at a flow rate of 0.25 L/minute in a Westfalia KA2 centrifuge containing four chambers. Two separate centrifugations were performed producing two paste sublots containing the M-CSF refractile bodies. The sublots were resuspended and agitated in a 1% (v/v) Triton® X-100/citrate buffer and centrifuged using a Sorvall RC-3B centrifuge at 5,000 g for 40 minutes. The pellets were combined and resuspended in approximately 5 L of 50 mM acetate, 2 mM EDTA, 0.5M NaCl buffer at pH 6.0, and diafiltered against 10 volumes of the same buffer using a 0.2 μm pore size, mixed cellulose acetate/nitrate hollow fiber system (10 ft$^2$). This was followed by a further 5 diafiltration volumes of DI water. The suspension was harvested from the system, mixed with DI water used to flush the system, and then centrifuged. The resulting pellet was stored at −70° C. until required for purification.

Compared to the first generation process, the throughput of M-CSF was increased by a factor of 3 and had a higher recovery efficiency. The protein/dry weight value of the new process was 92% (psd 3.9%) as shown in Table 1. The level of total nucleic acid in the final pellet was less than 1% of the dry weight. The total DNA plus RNA per M-CSF in the old process was 2.97% while in the new process it was 0.29%, about a 10-fold decrease.

TABLE I

Comparison of the '700 and the Present Process Up to Step 9

|  | '700 | Present |
|---|---|---|
| M-CSF Yield (g) | 45 | 120 |
| M-CSF % Recovery (% g/g) | 45 | 53.5 |
| % Protein/Dry Weight (% g/g) | 90 | 92 |
| % DNA & RNA/CSF (% g/g) | 2.97 | 0.29 |

Example 3

1000 Liter Scale

This is an example of process steps 1 through 9 as shown in scheme 1, on page 30, at the 1000 L scale.

The process scheme is illustrated in FIGS. 1 and 1A. *E. coli* DG116 containing plasmid pLCSF221A were grown at 30° C., induced at 38.5° C. at an $OD_{680}$ of 25 and harvested 6 hours post-induction. Nutrient concentrations and other fermentation details are essentially similar to those described in text above. The cells were chilled to 15°–20° C. and concentrated to 20–25% of the original volume by microporous cross-flow filtration. The residual fermentation broth containing divalent cations was removed in the subsequent diafiltration against 1000 L of 100 mM citrate, 2 mM EDTA, pH 6.5 in the same diafiltration system. The diafiltered suspension was homogenized at 7500 psig in a M12 gaulin homogenizer, 3 passes, 15°–20° C. The homogenate was made 1% v/v in 1-octanol to inactivate residual live recombinant *E. coli* cells and kept overnight at 15°–20° C. The treated homogenate was made 12% wt/v in sucrose and centrifuged at a flow rate of 2.5–3.0 L/minute in a Sharples AS16 centrifuge. Four to five separate centrifugations were performed producing paste sublots containing the M-CSF refractile bodies. The sublots were resuspended in 100 volumes 1% (v/v) Triton® X-100/citrate buffer and centrifuged using Sharples AS16, 15500 g. The pellets were combined and resuspended in approximately 30–50 L of 50 mM acetate, 2 mM EDTA, 0.5M NaCl buffer at pH 6.0, and diafiltered against 10 volumes of the same buffer. This was followed by a further 5 diafiltration volumes of DI water. The suspension was concentrated in the system and harvested. The resulting paste was stored at −70° C. until required for purification.

Example 4

Purification of RBs According to '700

M-CSF RB were purified according to the prior process shown in example 5 of U.S. Pat. No. 4,929,700, starting at Column 17, line 40. However, the following differences were noted: one 10×45 DEAE column was used in lieu of two 5×45 columns (see column 17, line 53); the $A_{280}$ was 1 (see column 18, line 11); the sodium phosphate concentration was 0.025M (see column 18, line 18); and ethylene glycol was not used.

Example 5

Preparation of RBs According to the Present Process (100 L)

The following is an example of process steps 10 to 22 as shown in scheme 1 and 1A, on pages 30–31, and is called the downstream process.

411 g of the frozen M-CSF RB paste from Example 2 were thawed and resuspended in 12,000 ml of buffer (25 mM EDTA, 0.1M Tris-HCl pH 8.5) and the mixture was homogenized. 1.8 g of DTT was added to achieve a concentration of 10 mM and then the mixture was poured into a 16M urea slurry for a final concentration of 5 mM DTT and 8M urea. Subsequently, the mixture was heated to 21° C.±3° C., then stirred for between 45 and 60 minutes. This denatured and reduced the protein (M-CSF RB) (the solution had a total optical density of 76,144 O.D. at A280 nm; this number was used to measure approximate total protein concentration and to track the reproducibility of the process). This denatured/reduced protein solution (M-CSF monomer mixture) was filtered through a 1.2 to 0.45 μm capsule filter.

A DEAE Zeta-Prep cartridge was pre-equilibrated with 0.1M sodium chloride, 25 mM EDTA, 0.5M Tris-HCl, pH 8.5. Then, the cartridge was equilibrated with an equilibration buffer containing 0.05M sodium chloride, 8M urea, 12.5 mM EDTA, 5 mM DTT, 0.05M Tris-HCl, at a pH of 8.5. 9.07 g of sodium chloride was added to the protein solution (M-CSF monomer mixture) to increase its conductivity. The protein solution (M-CSF monomer mixture) was then pumped through the DEAE Zeta-Prep cartridge at 100 ml/minute and the M-CSF was recovered in the filtrate. After pumping, the cartridge was flushed with 800 ml of the equilibration buffer and pooled (the solution had a total protein concentration of 67,939 O.D. or 20.65 O.D./ml). The pooled protein solution (M-CSF monomer mixture) was cooled to 4° C. and added to cold (4° C.) refolding buffer (5 mM of EDTA in 50 mM Tris-HCl, pH 8.5; reduced glutathione was added just before addition to the protein solution to a final concentration of 0.4 mM and oxidized glutathione was added to a final concentration of 0.2 mM; final concentration is measured after the protein solution has been added) at a rate of 11 ml/minute at 4° C. to achieve 1 OD/ml (the total volume was 64,334 ml). The mixture was stirred for approximately 89 hours.

The resulting protein solution (M-CSF pool) was then concentrated and diafiltered as follows. The pH was adjusted to 7.0±0.2 with 1,352 ml (2% of the total volume) of 1M NaH$_2$PO$_4$ and 1,352 ml of 1N HCl. This solution (M-CSF pool) was concentrated to 7.3 OD/ml by ultrafiltration. The solution (M-CSF pool) was then diafiltered against 81 L of 20 mM sodium phosphate buffer at pH 7.0 (total protein was measured as 61,359 O.D. or 7.3 OD/ml). 168 ml of 10 mM CuCl$_2$ (to a final concentration of 0.2 mM) were added to oxidize the protein (M-CSF pool) a second time and it was allowed to stand at 4° C. for 17 hours to ensure complete oxidation. Thereafter, a DEAE-Sepharose Fast Flow column (Amicon 18×28 cm) was equilibrated with 20 mM phosphate buffer at pH 7.0 and the total volume (8,424 ml) of the oxidized protein solution (M-CSF pool) was loaded onto the column at 100 ml/minute. The product was eluted with a gradient of 0.0>0.4M sodium chloride in 20 mM phosphate buffer, pH 7.0. The fractions containing the dimeric M-CSF were pooled to produce a total OD of 18,056 or 3.75 OD/ml.

The DEAE M-CSF pool was diluted to 1.0 OD (to a final volume of 17,993 ml) with 20 mM phosphate buffer at pH 7 and between 2°–8° C. 3,087 g of (NH$_4$)$_2$SO$_4$ was added to achieve a 1.2M solution. This solution was stirred from between 30 and 60 minutes and then filtered through a 1.2–0.45 μm filter (total protein measured as 17,472 OD or 0.84 OD/ml). A Phenyl Sepharose Fast Flow 18 ×15 cm column was equilibrated with 1.2M (NH$_4$)$_2$SO$_4$, 10 mM phosphate buffer, at pH 7.0. The entire pool (20,785 ml of the (NH$_4$)$_2$SO$_4$ filtrate) was added onto the column at 100 ml/minute. The product (M-CSF dimer) was eluted with a gradient of 0.8M >0.0M (NH$_4$)$_2$SO$_4$ in 10 mM phosphate buffer. The fractions containing the dimeric M-CSF were pooled to achieve a 15,950 mg having a total OD of 10,675 or 3.01 mg/ml. The pool was then concentrated by ultrafiltration to not less than 6.5 mg/ml protein, then diafiltered against not less than 7 volumes of 6 mM sodium citrate at pH 7.0 (15,152 mg, 6.42 mg/ml).

The following table illustrates M-CSF recoveries obtained in the prior ('700) and the present processes.

TABLE II

| STEP | Comparison of Downstream Process Yields | |
|---|---|---|
| | '700 Process | Present Process |
| Denaturation of RBs (start of downstream process) | 8.2 g M-CSF | 35 g M-CSF |
| Formulation Pool | 1.3 g M-CSF | 15.9 g M-CSF |
| Total Recovery | 15.9% | 45.4% |

In comparison, it is shown that the present downstream process recovers substantially more M-CSF than the '700 process (approximately 3-fold). Furthermore, when the present upstream process (Example 2, steps 1 to 9) is combined with the downstream process (this example, steps 10 to 22) the total increase in recovery is substantially greater than that of the '700 process.

Example 6

M-CSF Formulation

Purified M-CSF similar to that prepared in Example 5 was formulated for parenteral administration. The M-CSF protein pool was adjusted to obtain 4 mg/ml MCSF, 4% (wt/v) mannitol, 1% (wt/v) sucrose, 5 mM sodium citrate, and 0.5% (wt/v) glycine. The pH was adjusted to 6.5 with NaOH. Thereafter, the formulation was filtered through a 1.2 to 0.45 μm filter and lyophilized.

Example 7

M-CSF Lyophilization

A sample of the liquid formulation described above was loaded onto shelves that had been prechilled at a set point of −50° C. The temperature was held at −50° C. for 2 hours. The shelf temperature was raised to −15° C. at a rate of 60° C./hr (approximately 1 hour). The temperature was held at −15° C. for 1 hour and the condenser was cooled to below −60° C. The vacuum was pulled and maintained at 10±10 mmHg. The shelf temperature was raised to 30° C. at a rate of 45° C./hr (approximately 1 hour) and held for nine hours at 30° C. Then, the vials were stoppered under nitrogen pressure of 13.5 psia. No sign of collapse was observed; the appearance of the dried cake was very good. Moisture content was less than 1%. The lyophilized M-CSF sample contained 4 mg M-CSF, 40 mg mannitol, 10 mg sucrose, 0.96 mg sodium citrate, and 5 mg glycine.

FIG. 1 depicts the shelf and product temperature as well as the sample chamber pressure during the above lyophilization procedure.

Example 8

Preparation of RBs for Formulation (1000 L)

1. Fermentation and Harvest

A 1500 L fermentor was filled to a final volume of 1000 L with the following trace elements 60 μM ZnSO$_4$.7H$_2$O, 2 μM MnSO$_4$.H$_2$O, 2 μMCuSO$_4$ .5H$_2$O; 1.5 mM Na$_3$ citrate .2H$_2$O; 25 mM KH$_2$PO$_4$; 100 mM (NH$_4$)$_2$SO$_4$; and 0.02% (v/v) of media PPG (polypropylene gylcol). PPG was added throughout the fermentation as required to control the foam. The medium was sterilized in the fermentor, and the following ingredients were added aseptically to the following final concentrations: 100 μM FeSO$_4$. 7H$_2$O; 3 mM MgSO$_4$. 7H$_2$O; 20 mg/L thiamine. HCl. Glucose was added in three batches to a final concentration at each time of 20 g/L. The glucose was added at the beginning of fermentation, at induction, and some time 1 to 4 hours after induction. Then, the fermentor was inoculated with 2 mg/L (dry weight) of E. coli DG116/pLCSF 221A (ATCC No. 67,390, deposited Apr. 14, 1987), a bacterium which contains a plasmid encoding a long form of M-CSF monomer (see U.S. Ser. No. 07/105,261).

The culture was fermented at 30° C., and once the OD$_{680}$ reached 25, the temperature was shifted to 38.5° C. to induce expression. Casamino acids were added to a final concentration of 2% (wt/v) at induction.

Six hours after induction, the cells were harvested by (1) concentration of the cells, and (2) removal of unwanted media components. The microorganisms were concentrated four fold by cross flow filtration with a 0.2 μm PTFE flat sheet membrane utilizing a transmembrane pressure differential of about 20 psi. Further, unwanted media components were removed and the ionic strength was lowered by diafiltering the microorganisms containing M-CSF RB utilizing a 0.2 μm PTFE flat sheet with transmembrane pressure differential of about 20 psi versus 0 volumes of 100 mM sodium citrate, 2 mM EDTA at pH 6.5.

2. Primary Recovery

The bacteria M-CSF RB was disrupted by homogenization at 7500 psig, by three discrete passes at ~10°–15° C.).

Next, as a safety precaution, the remaining unlysed microorganisms containing M-CSF RB were killed by adding 1-octanol to a final concentration a 1% (v/wt). The bacteria containing M-CSF RB were incubated for one hour in the 1-octanol.

Sucrose was added to a final concentration of 12% (wt/v) to create a homogeneous sucrose cushion. The homogeneous sucrose cushion was centrifuged in a Sharples AS16 centrifuge at 15,500 g at a flow rate of 2–3 L/min. The centrifuge was stopped periodically to collect the M-CSF RB from the centrifuge bowl. The M-CSF RB were resuspended in 1% (v/v) Triton® X-100, 100 mM sodium citrate at pH 6.5. The resuspended M-CSF RB were centrifuged in a Sharples AS16 centrifuge at 15,500 g at a flow rate of 2–3 L/min, and the M-CSF RB were recovered in the pellet phase. Preferably, the M-CSF RB were diafiltered using a 0.2 µm mixed cellulose ester hollow fiber membrane with transmembrane pressure differential of 10 psi. The M-CSF RB were resuspended in an acetate/salt buffer of 50 mM sodium acetate, 0.5M NaCl, 2 mM EDTA, pH 6.0. The resuspended M-CSF RB were diafiltered against 10 volumes of the above acetate/salt buffer using a 0.2 µm mixed cellulose ester hollow fiber membrane with a transmembrane pressure differential of 5–20 psi. The unwanted supernatant was removed by concentrating the diafiltered M-CSF RB by ultrafiltration by 5 fold using the diafiltration configuration.

3. Solubilization and Denaturation of RB

The M-CSF RB paste was thawed and solubilized and denatured in 6M guanidine hydrochloride, 5 mM dithiothreitol (DTT), 25 mM EDTA, 0.1M Tris at pH 8.5. The Tris-base was added in its crystalline form to prevent further dilution of the M-CSF RB paste. The M-CSF RB paste was suspended with a Tekmar homogenizer. The M-CSF RB paste was incubated in the solubilization solution at 21°±1° C. for 45–60 minutes. The resulting M-CSF monomer mixture was sterile filtered.

Next, the M-CSF monomer mixture was diafiltered against three different buffers using a 30 KD MWCO membrane of regenerated cellulose. Further, the M-CSF monomer mixture was diafiltered using by cross-flow filtration with a plate and frame diafiltration configuration. Applicants carefully chose the membrane pore size to minimize the loss of M-CSF monomer but maximize the throughput time. The pore size is larger than the M-CSF monomer, but only 10% of the M-CSF monomer is lost.

The M-CSF monomer mixture was first diafiltered against at least a minimum of 2.5 volumes of 6M guandine hydrochloride, 5 mM DTT, 10 mM EDTA, 50 mM Tris pH 8.5 using the above filtration configuration. The M-CSF monomer mixture was diafiltered against 2.5 volumes of a second diafiltration buffer of 3 mM DTT, 10 mM EDTA, and 50 mM Tris pH 8.5 using the above filtration configuration. The M-CSF monomer mixture was diafiltered against at least 2.5 volumes of 8.67M Urea, 3 mM DTT, 10 mM EDTA, and 50 mM Tris pH 8.5 using the above filtration configuration.

4. Refolding-Oxidation

Five liters of diafiltered M-CSF monomer mixture was pumped at a flow rated of 8–12 mL into 95 L of redox buffer of 0.4 mM reduced glutathione, 0.2 mM oxidized glutathione, 5 mM EDTA, and 50 mM Tris-HCl pH 8.5. The oxidized and reduced glutathione was added last before the M-CSF monomer mixed was pumped into the redox buffer.

The M-CSF monomer/redox mixture was incubated at 2°–8° C. for 4 days for maximal refolding, oxidation, and yield of M-CSF biological activity. The resulting mixture is called the M-CSF pool.

After the primary oxidation step, the pH of the M-CSF pool was adjusted to 7.0, with 1M $NaH_2PO_4$ and 1N HCl. Next, the M-CSF pool was concentrated and diafiltered to an $A_{280}$ of 5 with a 10 kD polysulfone membrane using a hollow fiber, polysulfone or regenerated cellulose membrane, filter configuration with a transmembrane pressure differential of 15–20 psi against 10 volumes of 20 mM $NaPO_4$, pH 7.0. The resulting M-CSF pool is oxidized a second time overnight at 4° C. by adding $CuCl_2$ to a final concentration of 0.2 mM.

After the secondary oxidation, the M-CSF pool was ultrafiltered with a 300 KD MWCO polysulfone membrane with a transmembrane pressure differential of 15–20 psi. The M-CSF pool was ultrafiltered to 1 L and then diafiltered with 10 volumes of 20 mM $NaPO_4$, pH 7.0. Permeate from the ultrafiltration and the diafiltration was combined and to be loaded onto the DEAE column.

5. Column Chromatography and Purification

The ultrafiltered M-CSF pool that was subjected to secondary oxidation was loaded onto a DEAE-Sepharose ion exchange column, equilibrated with 20 mM NaPO4, pH 7.0. Protein was eluted from the column with with a 0.0–0.4M NaCl linear gradient in 20 mM $NaPO_4$ at pH 7.0. The M-CSF dimer size was used as a cutoff to determine the fractions to retain. These fractions were pooled and subjected to ammonium sulfate precipitation to remove the unstable M-CSF conformer, residual monomer, and oligomers from the active M-CSF dimers. Ammonium sulfate, $(NH_4)_2SO_4$, is added to a final concentration of 1.2M. The ammonium precipitated mixture was filtered with two filters, 1.2 and 0.45 µm, sandwiched together to remove the precipitants, and the filtrate is loaded onto a Phenyl-Sepharose column, equilibrated with 0.8M $(NH_4)_2SO_4$, 10 mM $NaPO_4$, pH 7.0. The M-CSF dimer was eluted from the column with a 0.8 to 0.15M $(NH_4)_2SO_4$ linear gradient in 10 mM $NaPO_4$ at pH 7.0. The fractions containing M-CSF dimer were pooled and sterile filtered. The M-CSF dimer filtrate was diafiltered with a 10 kD polysulfone hollow fiber using a transmembrane pressure differential of 15–20 psi against 10 volumes of 6 mM sodium citrate, pH of 6.5. The product from the diafiltration is called the purified M-CSF pool.

The present invention has been described with reference to specific embodiments. However, this application is intended to cover those changes and substitutions which may be made by those skilled in the art without departing from the spirit and the scope of the appended claims.

We claim:

1. A process for purifying macrophage colony stimulating factor (M-CSF) from bacterial contaminants, including proteins, nucleic acids, and non-proteinaceous compounds, when the M-CSF has been produced in the form of refractile bodies, the process comprises:

a) isolating M-CSF containing refractile bodies from bacteria;

b) suspending and agitating the refractile bodies in 1% (v/v) Triton® X-100 and sodium citrate;

c) centrifuging the suspended and agitated refractile bodies;

d) resuspending the centrifuged refractile bodies in sodium acetate, NaCl, and ethylenediaminetetroacetic acid (EDTA);

e) diafiltering the refractile body suspension from step (d) against sodium acetate, NaCl, and EDTA and subsequently diafiltering the refractile body suspension against water; and f) recovering the refractile bodies from step (e) for further treatment.

2. A process in accordance with claim 1, wherein step (a) comprises: producing refractile bodies by fermenting bacteria containing M-CSF DNA, killing the bacteria by adding octanol, and separating the refractile bodies from the cellular debris by centrifugation in 12% (wt/v) sucrose.

3. A process in accordance with claim 2 further comprising:

g) solublizing and denaturing the refractile bodies from step (f) in 8M Urea, 5 mM dithiothreitol (DTT), 25 mM EDTA, and 0.1M Tris, at pH 8.5;

h) filtering the solution from step (g), then subjecting the filtrate to diethylaminoethyl (DEAE) chromatography in 50 mM NaCl, 8M Urea, 12.5M EDTA, 5 mM DTT, and 5 mM Tris, at pH 8.5;

i) refolding and oxidizing the M-CSF from step (h) in 0.4 mM reduced glutathione, 0.2 mM oxidized glutathione, 50 mM Tris-HCl, and 5 mM EDTA, at pH 8.5 and 2°–8° C. for 4 days;

j) adjusting the pH of the solution from step (i) to 7 and concentrating the solution;

k) reoxidizing the M-CSF from step (j) in 0.2 mM $CuCl_2$ and 20 mM sodium phosphate;

l) filtering the solution from step (k) then chromatographing the filtrate on DEAE-Sepharose ion exchange chromatography;

m) precipitating unstable M-CSF from step (l) by adding 1.2M ammonium sulfate and filtering the precipitate;

n) chromatographing the filtrate from step (m) on a Phenyl-Sepharose column; and o) diafiltering the M-CSF from the step (n) with not less than 7 times the M-CSF volume of a pH 7.0 sodium citrate/sodium chloride solution.

4. A process in accordance with claim 3, wherein the optical density (OD) of the solution containing the M-CSF in step (j) is adjusted to between 0.2 and 2.0

5. A process in accordance with claim 3, wherein the OD of the solution containing the M-CSF in step (j) is adjusted to between 0.75 and 1.5.

6. A process in accordance with claim 3, wherein the OD of the solution containing the M-CSF in step (j) is adjusted to about 1.

7. A process in accordance with claim 1, wherein the refractile bodies in step a) are agitated in 1% (v/v) Triton® X-100 and 100 mM sodium citrate, at pH 6.5; and the solutions of steps d) and e) are 50 mM sodium acetate, 0.5M NaCl, and 2 mM EDTA.

8. A process for producing and purifying M-CSF from bacterial proteins, nucleic acids, and lipids when the M-CSF has been produced in the form of refractile bodies, the process comprises:

a) fermenting bacteria containing M-CSF DNA so that the bacteria express the M-CSF as refractile bodies;

b) killing the bacteria by adding octanol;

c) separating the refractile bodies from the cellular debris by centrifugation in 12% (wt/v) sucrose;

d) suspending and agitating the refractile bodies from step (c) in 1% (v/v) Triton®-X 100 and 100 mM sodium citrate, at pH 6.5;

e) centrifuging the refractile bodies from step (d);

f) resuspending the centrifuged refractile bodies in 50 mM sodium acetate, 0.5 M NaCl, and 2 mM EDTA at pH 6.0;

g) diafiltering the refractile body suspension from step (f) against 50 mM sodium acetate, 0.5M NaCl, and 2 mM EDTA and then water;

h) centrifuging the refractile bodies from step (g);

i) recovering the refractile bodies from step (h);

j) solubilizing and denaturing the refractile bodies from step (i) in 8M Urea, 5 mM DTT, 25 mM EDTA, and 0.1M Tris, at pH 8.5;

k) filtering the solution from step (j), then subjecting the filtrate to DEAE chromatography in 50 mM NaCl, 8M Urea, 12.5 mM EDTA, 5 mM DTT, and 5 mM Tris, at pH 8.5;

l) refolding and oxidizing the M-CSF from step (k) in 0.4 mM reduced glutathione, 0.2 mM oxidized glutathione, 50 mM tris-HCl, and 5 mM EDTA, at pH 8.5 and 2°–8° C. for 4 days;

m) adjusting the pH of the solution from step (l) to 7 and concentrating the solution by diafiltration;

n) reoxidizing the M-CSF from the step (m) in 0.2 mM $CuCl_2$ and 20 mM sodium phosphate;

o) filtering, then chromatographing the M-CSF from step (n) with DEAE-Sepharose ion exchange chromatography;

p) precipitating unstable M-CSF from the solution of step (o) by adding 1.2M ammonium sulfate and filtering the precipitate;

q) chromatographing the filtrate from step (p) on a Phenyl-Sepharose column; and r) diafiltering the M-CSF from step (q) with not less than 7 times the M-CSF volume of a pH 7.0 sodium citrate chloride solution.

9. A process in accordance with claim 8, wherein the OD of the solution containing the M-CSF in step (l) is adjusted to between 0.2 and 2.0.

10. A process in accordance with claim 8, wherein the OD of the solution containing the M-CSF in step (l) is adjusted to between 0.75 and 1.5.

11. A process in accordance with claim 8, wherein the OD of the solution containing the M-CSF in step (l) is adjusted to about 1.

12. A process for purifying M-CSF dimer from microorganisms containing M-CSF refractile bodies, wherein the process comprises:

a) lysing microorganisms containing M-CSF refractile bodies;

b) exposing the lysed microorganisms to an effective amount of 1-octanol to kill the remaining viable microorganisms;

c) centrifuging the lysed microorganisms of step (b) in an effective homogenous sucrose cushion to form a pellet containing M-CSF refractile bodies, wherein the homogenous sucrose cushion comprises about 12% (wt/v) sucrose;

d) recovering the pellet from the homogenous sucrose cushion;

e) washing the pellet containing M-CSF refractile bodies with an effective amount of a non-ionic detergent to remove contaminants, wherein between about 1% and about 2% (v/v) of the non-ionic detergent Triton®

X-100 is used;

f) solubilizing and denaturing the M-CSF refractile bodies from step (e) to form a mixture of M-CSF monomers;

g) refolding the M-CSF monomers from step (f) under refolding conditions to form M-CSF dimers; and h) purifying the M-CSF dimers from step (g).

13. A process for lyophilizing a liquid M-CSF formulation, wherein the process comprises:

(a) providing a liquid M-CSF formulation comprising M-CSF dimer, and effective concentration of mannitol to provide an effective amount of crystallized mannitol, and an effective amount of amorphous protectant to reduce the physical and chemical alterations of the M-CSF dimer;

(b) freezing the liquid M-CSF formulation to form a frozen product comprising an effective amount of crystallized mannitol to provide for sublimation;

(c) sublimating the water from the frozen product under subatomspheric conditions by raising the frozen product temperature to a final product temperature without a constant drying period.

14. The process in accordance to claim 13, wherein the liquid M-CSF formulation of step (a) comprises 1 to 25 mg/ml of M-CSF dimer, 3 to 4% (wt/v) of mannitol, 0.75 to 1.25% (wt/v) sucrose, 0.3 to 0.7% (wt/v) glycine, and 4 to 6 mM sodium citrate, at pH 6.5.

15. The process in accordance to claim 14, wherein step (b) further comprises:

(i) lowering the liquid M-CSF formulation temperature to between −40° and −60° C. to form a frozen product; and (ii) rasing the frozen product temperature to between −25° and −12° C. to crystallize an effective amount of mannitol to provide for sublimation.

16. The process in accordance to claim 15, wherein step (c) further comprises:

(i) raising the frozen product temperature to a final product temperature between about 20° and about 40° C.; and (ii) maintaining the final product temperature for 7 to 20 hours.

17. A process for lyophilizing a liquid M-CSF formulation in a lyophilizer that comprises an enclosed sample chamber having a shelf, wherein the chamber is operably linked to a means to condense water and a means to reduce the chamber pressure, and the shelf is operably connected to a means to control the shelf temperature, wherein the process comprises:

(a) placing a liquid M-CSF formulation comprising M-CSF and an effective amount of mannitol to provide an effective amount of crystallized mannitol on the shelf;

(b) freezing the liquid M-CSF formulation to form a frozen product comprising an effective amount crystallized mannitol to provide for sublimation;

(c) reducing the chamber pressure to subatmospheric pressures following step (b);

(d) under reduced chamber pressure, raising the shelf temperature to a final product temperature without a constant drying period; and (e) maintaining the shelf temperature at the final product temperature under reduced chamber pressure.

18. A process in accordance to claim 17, wherein the liquid M-CSF formulation of step (a) comprises 1 to 25 mg/ml of M-CSF, 3 to 4% (wt/v) mannitol, 0.75 to 1.25% (wt/v) sucrose, 0.3 to 0.7% (wt/v) glycine, and 4 to 6 mM sodium citrate, at pH 6.5.

19. A process in accordance to claim 18, wherein step (b) further comprises:

(i) lowering the shelf temperature to between about −40° and about −60° C. to form a frozen product; and (ii) raising the shelf temperature to between about −25° and about −12° C. to crystallize an effective amount of mannitol to provide for sublimation.

20. A process in accordance to claim 19 that further comprises cooling the means to condense water to below about −60° C. after step (b).

21. A process in accordance to claim 20, wherein the chamber pressure is reduced at step (e) to between about 100 and about 200 μmHg, and the final product temperature is between about 25° C. and about 35° C.

22. A process in accordance to claim 21, wherein the shelf temperature in step (d) is raised at a rate of about 45° C./hour, and the shelf temperature in step (e) is maintained for about 7 to about 20 hours.

23. A process in accordance to claim 22, wherein the liquid M-CSF formulation comprises 4 mg/ml of M-CSF, 4% (wt/v) mannitol, 1% (wt/v) sucrose, 0.5% (wt/v) glycine, 5 mM sodium citrate, and is adjusted to pH 6.5 with NaOH;

the shelf temperature in step (b) is about −50° C.;

the chamber pressure in step (c) is reduced to 100±10 μmHg; and the final product temperature in step (d) is about 30° C.

* * * * *